United States Patent [19]

Marsili

[11] Patent Number: 4,904,776
[45] Date of Patent: Feb. 27, 1990

[54] METHOD FOR PRODUCING CRYSTALLINE CEFADROXIL HEMIHYDRATE

[75] Inventor: Leonardo Marsili, Milan, Italy

[73] Assignee: Rifar S.R.L., Milan, Italy

[21] Appl. No.: 89,168

[22] Filed: Aug. 25, 1987

[51] Int. Cl.$^4$ .................. C07D 501/04; A61K 31/545
[52] U.S. Cl. .................................................... 540/230
[58] Field of Search ......................... 540/230; 514/209

[56] References Cited

U.S. PATENT DOCUMENTS 4,504,697  3/1989  Bouzard .............................. 540/230

OTHER PUBLICATIONS

Pfeiffer et al., Jour. of Pharma. Sciences, vol. 59, No. 12, pp. 1810–1814 (1970).

Primary Examiner—Nicholas S. Rizzo
Attorney, Agent, or Firm—Oblon, Spivak, McClelland, Maier & Neustadt

[57] ABSTRACT

The invention relates to a method for producing crystalline cefadroxil hemihydrate. According to the method a cefadroxil solvate is slurried with a mixture methanol:isopropyl alcohol 30:70 to 70:30 by volume containing from 5% to 12% of water, a temperature from +45° C. to +55° C. and then isolating the so obtained crystalline compound.

2 Claims, No Drawings

METHOD FOR PRODUCING CRYSTALLINE CEFADROXIL HEMIHYDRATE

The present invention relates to a method for producing crystalline cefadroxil hemihydrate which is a compound having pharmacological properties, disclosed and claimed in the co-pending U.S. patent application No. 043,494 filed on Apr. 28, 1987 by the present applicants.

According to above mentioned patent application the crystalline cefadroxil hemihydrate (which is clearly and correctly identified) is obtained by slurrying a cefadroxil solvate with a mixture ethanol:isopropyl alcohol 30:70 to 50:50 by volume.

Further experiments now carried out by the present applicants have shown that the amount of isopropyl alcohol can be lower than that one specified in the mentioned prior application, namely that the range methanol:isopropyl alcohol can be up to 70:30 by volume.

Moreover, while from the original patent application it was apparent that the reaction had to take place in the presence of water, nothing was specifically stated as to the amount of water because all the experiments that the inventor had at that time made were successful and nothing left him to think that water had to be present in a critical amount.

Now, going on with his experiments, the inventor ascertained that the mixture methanol:isopropyl alcohol must contain water in an amount from 5% to 12%.

Consequently the present invention relates to a method for producing crystalline cefadroxil hemihydrate, according to which a cefadroxil solvate of dimethylacetamide, of N-methyl-2-pyrrolidone or of monomethylformamide is slurried with a mixture methanol:isopropyl alcohol 30:7: to 70:30 by volume containing from 5% to 12% of water, at a temperature in the range of about +45° C. to +55° C. and then isolating the so obtained crystalline cefadroxil hemihydrate.

The method will be described in more details in the following not limitative Examples.

EXAMPLE 1

Cefadroxil dimethylacetamide solvate (50 g) prepared according to Example 1 of U.S patent application No. 043,494 was slurried in a mixture of isopropyl alcohol (250 ml) and ethanol (120 ml) iñ the presence of 24 ml of water at a temperature of +48°:50° C.

After 120' the mixture was cooled to 10° C., filtered and washed with acetone to yield 34.5 g of crystalline cefadroxil hemihydrate.
K.F.: 2.8%
Methanol: 0.009%
Isopropyl alcohol: 0.17%
HPLC Assay: 99.1% on dry basis.

EXAMPLE 2

Cefadroxil monomethylformamide solvate (30 g) prepared according to Example 3 of the U.S. patent application No. 043,494 was slurried in 150 ml of a mixture 1:1 of methanol:isopropyl alcohol in the presence of 16 ml of water at +52° C.

After 70' at 52° C. the mixture was cooled to 10° C., filtered and washed with acetone to yield 23.2 g of crystalline cefadroxil hemihydrate.
K.F.: 2.9%
HPLC Assay: 99.6% on dry basis
Methanol: 0.008% Isopropyl alcohol: 0.15%

EXAMPLE 3

Cefadroxil 1-methyl-2-pyrrolidone solvate (30 g) prepared according to Example 6 of the U.S. patent application No. 043,494 was slurried in a mixture of 100 ml of isopropyl alcohol and of 50 ml of methanol in the presence of 19 ml of water at a temperature of 45°-48° C. for 100'. After cooling to 10° C. the mixture was filtered, the product washed with acetone and dried at 40° C.
Yield: 19.5 g of hemihydrate product
K.F.: 2.5%
HPLC Assay: 98.2% on dry basis
Methanol: 0.009%
Isopropyl alcohol: 0.18%

EXAMPLE 4

Cefadroxil dimethylacetamide solvate (40 g) was slurried in a mixture of isopropyl alcohol (100 ml), methanol (200 ml) and water (30 ml) at 18°-50° C.

After 120' the mixture was cooled to 10° C., filtered and washed with acetone to yield 26.8 g of crystalline cefadroxil hemihydrate.
K.F. 3.1%
HPLC Assay: 98.7% on dry basis
Methanol: 0.008%
Isopropyl alcohol: 0.02%

EXAMPLE 5

Cefadroxil monomethylformamide solvate (30 g) was slurried in a mixture of methanol (100 ml), isopropyl alcohol (47 ml) and water (13 ml) at 50° C. After 90' at 50° C. the mixture was cooled to 10° C., filtered and washed with acetone to yield 22.9 g of crystalline cefadroxil hemihydrate.
K.F. 3.0%
HPLC Assay: 99.1% on dry basis.
Methanol: 0.008%
Isopropyl alcohol: 0.010%

EXAMPLE 6

Cefadroxil 1-methyl-2-pyrrolidone solvate (30 g) was slurried in a mixture of metahnol (80 ml), isopropyl alcohol (60 ml) and water (10 ml) at 50° C. for 90'. After cooling to 10° C. the mixture was filtered, the product washed with acetone and dried at 40° C. to yield 19.1 g of crystalline cefadroxil hemihydrate.
K.F.: 2.9%
HPLC Assay: 98.9 on dry basis.
Methanol: 0.009%
Isopropyl alcohol: 0.16%

What is claimed is:
1. A method for producing crystalline cefadroxil hemihydrate, which comprises:
   (a) adding to an aqueous solution of cefadroxil prepared from 7-ADCA, a solvent selected from the group consisting of dimethylacetamide, N-methyl-2-pyrrolidone and monomethylformamide, while controlling the pH of the solution in the range of 5.5-6.0, to give the corresponding cefadroxil solvate which precipitates and is filtered off and dried, and
   (b) slurrying said dried solvate with a mixture of methanol:isopropyl alcohol 30:70 to 70:30 by volume containing about 5% to 12% of water, at a temperature in the range of about +45° C. to +55° C., wherein after the crystalline cefadroxil hemihydrate obtained is isolated from the reaction mixture.

2. The method of claim 1, wherein said water content is about 6.4% to about 12.6%.

* * * * *